(12) United States Patent
Fuhrer et al.

(10) Patent No.: US 7,019,286 B2
(45) Date of Patent: Mar. 28, 2006

(54) TIME-OF-FLIGHT MASS SPECTROMETER FOR MONITORING OF FAST PROCESSES

(75) Inventors: Katrin Fuhrer, Bern (CH); Marc Gonin, Bern (CH); Kent J. Gillig, College Station, TX (US); Thomas Egan, Houston, TX (US); Michael I. McCully, Houston, TX (US); John A. Schultz, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 49 days.

(21) Appl. No.: 10/689,173

(22) Filed: Oct. 20, 2003

(65) Prior Publication Data
US 2004/0113064 A1 Jun. 17, 2004

Related U.S. Application Data

(63) Continuation-in-part of application No. 10/155,291, filed on May 24, 2002, now Pat. No. 6,683,299.

(60) Provisional application No. 60/293,737, filed on May 25, 2001.

(51) Int. Cl.
*H01J 49/40* (2006.01)
(52) U.S. Cl. ....................... 250/287; 250/282
(58) Field of Classification Search ................ 250/282, 250/287, 288
See application file for complete search history.

(56) References Cited

U.S. PATENT DOCUMENTS

| 5,563,410 A | * | 10/1996 | Mullock | ...................... 250/288 |
| 5,644,128 A | | 7/1997 | Wollnik et al. | |
| 5,905,258 A | | 5/1999 | Clemmer et al. | |
| 6,031,227 A | * | 2/2000 | Becker et al. | ............... 250/287 |
| 6,229,142 B1 | | 5/2001 | Bateman et al. | |
| 6,331,702 B1 | | 12/2001 | Krutchinsky et al. | |

FOREIGN PATENT DOCUMENTS

WO   WO-9967801 A2   12/1999

OTHER PUBLICATIONS

McKnight et al., "Low-Field Drift Velocities and Reactions of Nitrogen Ions in Nitrogen," Physical Review vol. 164 No. 1, Dec. 5, 1967, pp. 62-70.
Fockenberg et al, "Repetitively Sampled Time-of -Flight Mass Spectrometry for Gas-Phase Kinetic Studies," Review of Scientific Instruments vol. 70 No. 8, Aug. 1999, pp. 3259-3264.

* cited by examiner

*Primary Examiner*—Nikita Wells
*Assistant Examiner*—Paul M. Gurzo
(74) *Attorney, Agent, or Firm*—Fulbright & Jaworski LLP

(57) ABSTRACT

Time-of-flight mass spectrometer instruments for monitoring fast processes using an interleaved timing scheme and a position sensitive detector are described. The combination of both methods is also described.

14 Claims, 9 Drawing Sheets

US 7,019,286 B2

TIME-OF-FLIGHT MASS SPECTROMETER FOR MONITORING OF FAST PROCESSES

This application is a continuation-in part of, and claims priority to, U.S. application No. 10/155,291, filed May 24, 2002 now U.S. Pat. No. 6,683,299, and to U.S. Provisional Application No. 60/293,737, filed May 25, 2001.

This work has been funded in whole or in part with Federal funds from the National Institutes of Health, Department of Health & Human Services, NIH Phase II Grant No. 2 R44 RR12059-02A2. The United States government may have certain rights in the invention.

FIELD OF THE INVENTION

The invention is a time-of-flight mass spectrometer (TOF) capable of monitoring fast processes. More particularly, it is a TOF for monitoring the elution from an ion mobility spectrometer (IMS) operated at pressures between a few Torr and atmospheric pressure. This apparatus is an instrument for qualitative and/or quantitative chemical and biological analysis.

BACKGROUND OF THE INVENTION

There is an increasing need for mass analysis of fast processes, which in part, arises from the popularity of fast multi-dimensional separations techniques like GC-TOF, Mobility-TOF, or EM-TOF, (electron monochromator) etc. In those methods, the TOF serves as a mass monitor scanning the elution of the analyte of the prior separation methods.

There are numerous other fields of application involving the investigation of fast kinetic processes. Two examples are the chemical processes during gas discharges, and photon or radiofrequency induced chemical and plasma ion etching. In the case of gas discharges one may monitor the time evolution of products before, during and after the abrupt interruption of a continuous gas discharge or during and after the pulsed initiation of the discharge. An analogous monitoring of the chemical processes in a plasma etching chamber can be performed. The time profile of chemical products released from a surface into a plasma can be determined either during and after the irradiation with laser pulses or before, during and after the application of a voltage which induces etching (e.g., RF plasma processing). A third such example is the time evolution of ions either directly desorbed from a surface by energetic beams of X-ray, laser photons, electrons, or ions. In addition, when the ions are desorbed from a surface there is usually a more predominant codesorption of non-ionized neutral elements and molecules whose time evolution can be monitored by first post ionizing neutral species which have been desorbed and then measuring mass separated time evolution of the ions by mass spectrometry. Yet a fourth area of use is the monitoring of the time evolution of neutral elements or molecules reflected after a molecular beam is impinged on a surface. The importance of such studies range from fundamental studies of molecular dynamics at surfaces to the practical application of molecular beam epitaxy to grow single crystalline semiconductor devices. A further application for fast analysis is presented by Fockenberg et al.

In all such studies the time evolution of ion signals which have been mass resolved in a mass spectrometer is crucial. TOF instruments have become the instrument of choice for broad range mass analysis of fast processes.

TOF instruments typically operate in a semi-continuous repetitive mode. In each cycle of a typical instrument, ions are first generated and extracted from an ion source (which can be either continuous or pulsed) and then focused into a parallel beam of ions. This parallel beam is then injected into an extractor section comprising a parallel plate and grid. The ions are allowed to drift into this extractor section for some length of time, typically 5 µs. The ions in the extractor section are then extracted by a high voltage pulse into a drift section followed by reflection by an ion mirror, after which the ions spend additional time in the drift region on their flight to a detector. The time-of-flight of the ions from extraction to detection is recorded and used to identify their mass. Typical times-of-flight of the largest ions of interest are in the range of 20 µs to 200 µs. Hence, the extraction frequencies are usually in the range of 5 kHz to 50 kHz. If an extraction frequency of 50 kHz is used, the TOF is acquiring a full mass spectrum every 20 µs. After each extraction, it takes some finite time for the ions of the primary beam to fill up the extraction chamber. This so-called fill up time is typically relatively shorter for lighter ions as compared to heavier ions because they travel faster in the primary beam. For light ions, the fill up time may be as short as 1 µs whereas for very large ions, the fill up time may exceed the 20 µs between each extraction, and hence those large ions never completely fill up the extraction region. The fill up time depends on the ion energy in the primary beam, the length of the extraction region and the mass of the ions.

Some fast processes, however, require monitoring with a time resolution in the microsecond range. For example, a species eluting from an ion mobility spectrometer may elute through the orifice within a time interval of 15 µs. If this species also has a small fill up time it is possible that this elution occurs between two TOF extractions in such a way that the TOF completely misses the eluting species.

Known techniques to solve this problem are based on increasing the extraction frequency. In general, the ion flight time in the TOF section will determine the maximum extraction frequency, shorter flight times yielding higher extraction rates. The ion flight time is shortened by either increasing the ion energy in the drift section, or by reducing the length of the drift section. Increasing the ion energy is the preferred method, because decreasing the drift length results in a loss of resolving power. However, because the relationship between ion energy E and the time-of-flight T is a square-root dependence, an increase in energy only leads to a minimal decrease in flight time:

$$T = \frac{a}{\sqrt{E}}$$

Thus, more effective methods and corresponding apparatuses for monitoring such fast ion processes while minimizing the loss in sensitivity that occurs when eluted ions are not counted by the detector are needed.

SUMMARY OF THE INVENTION

In one embodiment of the present invention, there is an apparatus comprising an ion source for repetitively generating ions; an ion-fragmentation device fluidly coupled to said ion source; an ion extractor, fluidly coupled to said ion fragmentation device and extracting said ions; a time-of-flight mass spectrometer fluidly coupled to and accepting ions from said ion extractor, a position sensitive ion detector fluidly coupled to said time-of-flight mass spectrometer to detect said ions; a timing controller in electronic communication with said ion source and said ion extractor said timing controller tracking and controlling the time of activation of said ion source and activating said ion extractor according to a predetermined sequence; and, a data processing unit for analyzing and presenting data said data processing unit in electronic communication with said ion source, said ion extractor, and said position sensitive ion detector.

In another embodiment of the apparatus, the ion fragmentation device is positioned to fragment ions at a location within the ion extractor or at a location before the ion extractor.

In another embodiment of the apparatus, the timing controller or the data processing unit or both are in electronic communication with said ion-fragmentation device.

In another embodiment of the present invention, there is method of determining the temporal profile of fast ion processes comprising: generating ions in an ion source; tracking the time of said step of generating by a timing controller; fragmenting said ions to form fragment ions; extracting said ions and fragment ions in a single or repetitive manner according to a predetermined sequence; separating said extracted ions and fragment ions in a time-of-flight mass spectrometer; detecting said ions and fragment ions with a position sensitive ion detector capable of resolving the location of impact of said ions and fragment ions onto said detector; analyzing the time characteristics of said fast processes from said impact location, the time from the step of tracking, and the time of activation of said extractor to determine the temporal profile of the fast ion processes.

In another embodiment of the method, the step of fragmenting said ions occurs in the ion extractor or upstream of the ion extractor.

In another embodiment of the method, the step of analyzing further comprises analyzing the time characteristics of said fast processes using the time of activation of said step of fragmenting.

In another embodiment of the present invention, there is an apparatus comprising an ion source capable of repetitively generating ions; an ion-fragmentation device fluidly coupled to the ion source and capable of generating fragment ions; an ion extractor, fluidly coupled to the ion-fragmentation device and extracting said ions and fragment ions; a time-of-flight mass spectrometer fluidly coupled to and accepting said ions and fragment ions from said ion extractor, an ion detector fluidly coupled to said time-of-flight mass spectrometer to detect said ions and fragment ions; and, a timing controller in electronic communication with said ion source and said ion extractor said timing controller tracking and controlling the time of activation of said ion source and activating said ion extractor according to a predetermined sequence said sequence having a time offset between the activation of said ion source and the activation of said ion extractor.

In another embodiment of the apparatus, the ion fragmentation device is positioned to fragment ions at a location within the ion extractor or at a location before the ion extractor.

In another embodiment of the apparatus, the timing controller is in electronic communication with said ion-fragmentation device.

In another embodiment of the present invention, there is a method of determining the temporal profile of fast ion processes comprising: generating ions from an ion source; extracting said ions in a single or repetitive manner; activating said step of generating ions and said step of extracting said ions by a timing controller wherein said timing controller operates according to a predetermined sequence and further wherein said timing controller operates by a time offset between said step of activating and said step of extracting; fragmenting said ions before they are extracted into the time-of-flight mass spectrometer separating the ions and fragment ions according to their time-of-flight in a time-of-flight mass spectrometer; detecting the mass separated ions and fragment ions; analyzing the time characteristics of said fast ion processes from the time of said steps of activating, extracting, and detecting to determine the temporal profile of the fast ion processes.

In another embodiment of the method, the step of fragmenting said ions occurs in the ion extractor or upstream of the ion extractor.

In another embodiment of the method, the step of analyzing further comprises analyzing the time characteristics of said fast processes using the time of activation of said step of fragmenting.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The following discussion contains illustration and examples of preferred embodiments for practicing the present invention. However, they are not limiting examples. Other examples and methods are possible in practicing the present invention.

As used herein the specification, "a" or "an" may mean one or more. As used herein in the claim(s), when used in conjunction with the word "comprising", the words "a" or "an" may mean one or more than one. As used herein "another" may mean at least a second or more.

The following discussion contains illustration and examples of preferred embodiments for practicing the present invention. However, they are not limiting examples. Other examples and methods are possible in practicing the present invention.

Figure 2:
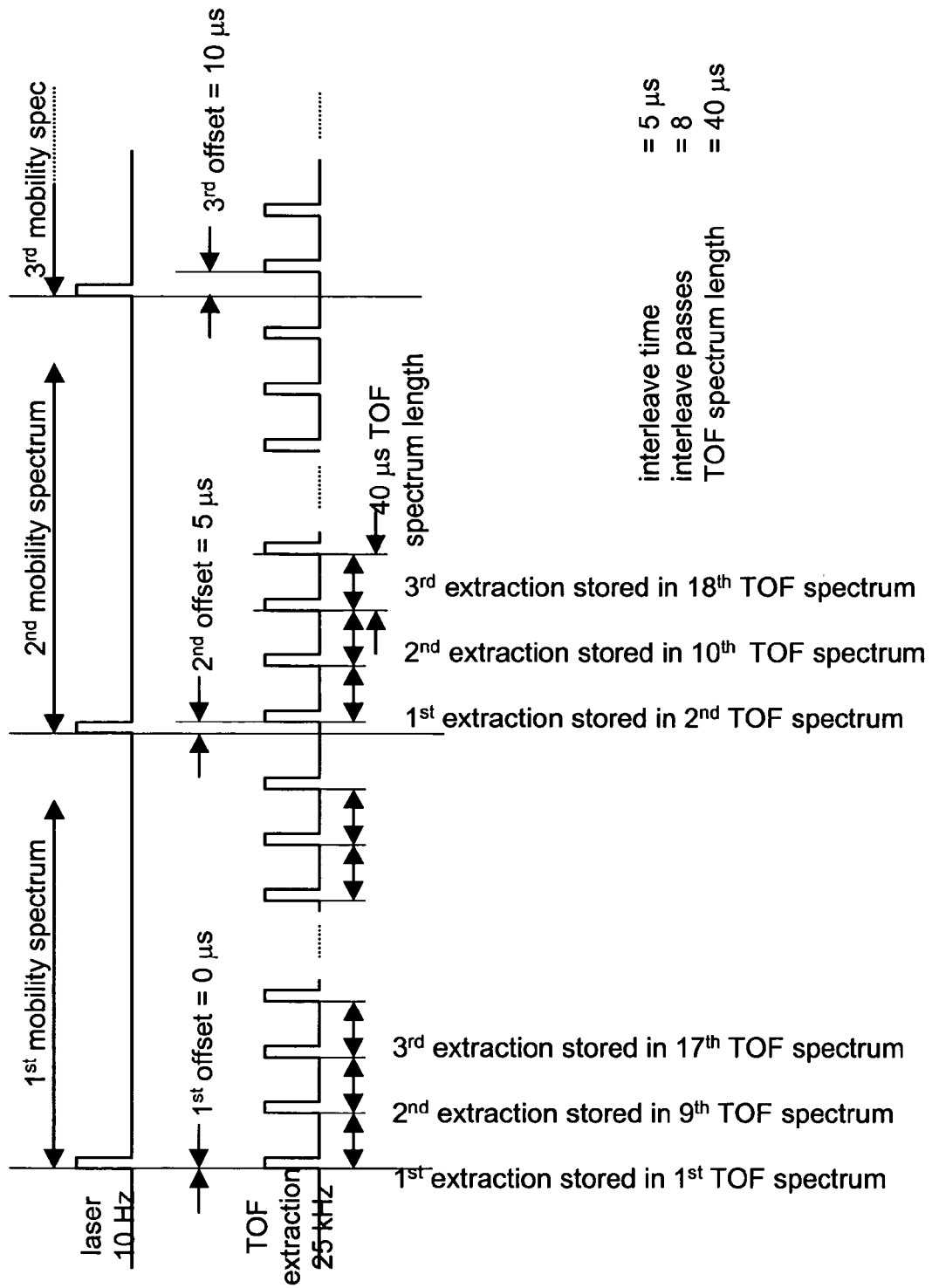
FIG. 2. Illustrative timing scheme of the interleaved TOF acquisition.

As defined herein, "interleaved timing sequence" is defined as a timing sequence that controls an interleaved data acquisition. Interleaved data acquisition refers to a method where the data points of a time series are reconstructed from measurements of several passes through the series. For example, the odd data points of a time series may be acquired in the first pass (i.e. data points 1,3,5,7, . . . ) and the even data points are acquired in the second pass (data points 2,4,6,8, . . . ). The essence of the interleaved method is the time offset between ion generation and ion extraction. The different data time points are collected through the use of such a time offset. Interleaved timing is therefore synonymous with a time offset between ion generation and extraction. In this way, the temporal profile is thus reconstructed. The time offset of FIG. 2 illustrates one example of an interleaved timing sequence where the time series is composed from acquisitions from 8 passes. The actual times in any analysis may vary from the illustrated values in the figure. The range of times can be large and generally vary from 0 to 1000 µs.

As used herein, "IMS" is defined as an ion mobility spectrometer. An ion mobility spectrometer consists of a drift tube in which ions traveling in a gaseous medium in the presence of an electric field are separated according to their ion mobilities. The ion mobilities of specific ion species result from the conditions of drift tube pressure and potential of the ion mobility experiment. The repetitive accelerations in the electric field and collisions at the molecular level result in unique ion mobilities for different ion species.

As used herein, "IMS/MS" is a combination of an ion mobility spectrometer and a mass spectrometer. A mass spectrometer separates and analyzes ions under the influence of a potential according to their mass to charge ratios.

As used herein, "IMS/IFP/MS" is a combination of an ion mobility spectrometer and a mass spectrometer with an ion fragmentation process between them. The ion fragmentation process can be any of those commonly known in the mass spectrometric art.

As used herein, "position sensitive ion detector", or PSD, is defined as an ion detector having the ability to detect the location of the analyte species within the detector at the time of detection. This is contrasted to detectors in which only the presence but not the location of the analyte within the detector is detected. The term "position sensitive ion detector" is synonymous with "position sensitive detection means" and "position sensitive detector" and may include, but is not limited to, meander delay line detectors, multiple meander delay line detectors, and multi-anode detectors in which the individual anodes may be of the same or different sizes.

As used herein, "time resolving power" is defined as the time of ion release by a process and the accuracy with which this release time can be determined. This is expressed mathematically as $T/\Delta T$ where T is the time of ion release in the process and $\Delta T$ is the accuracy of the measurement of T. It is used synonymously with "temporal resolving power".

As used herein, "TOF" is defined as a time-of-flight mass spectrometer. A TOF is a type of mass spectrometer in which ions are all accelerated to the same kinetic energy into a field-free region wherein the ions acquire a velocity characteristic of their mass-to-charge ratios. Ions of differing velocities separate and are detected.

Figure 1:
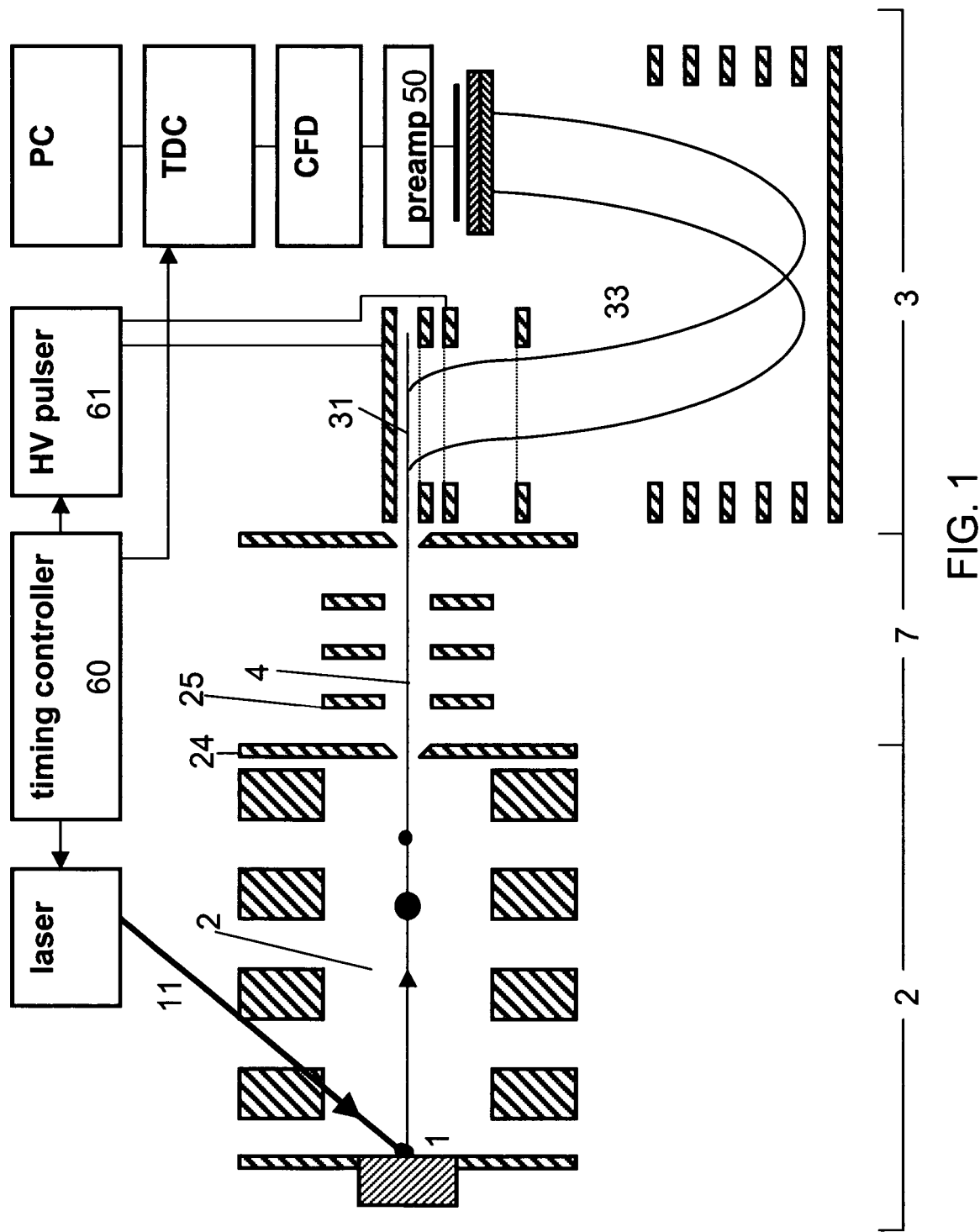
FIG. 1. Mobility-TOF comprising the basic architecture of the present invention. The interleaved timing scheme is used with this instrumental platform.
Figure 3:
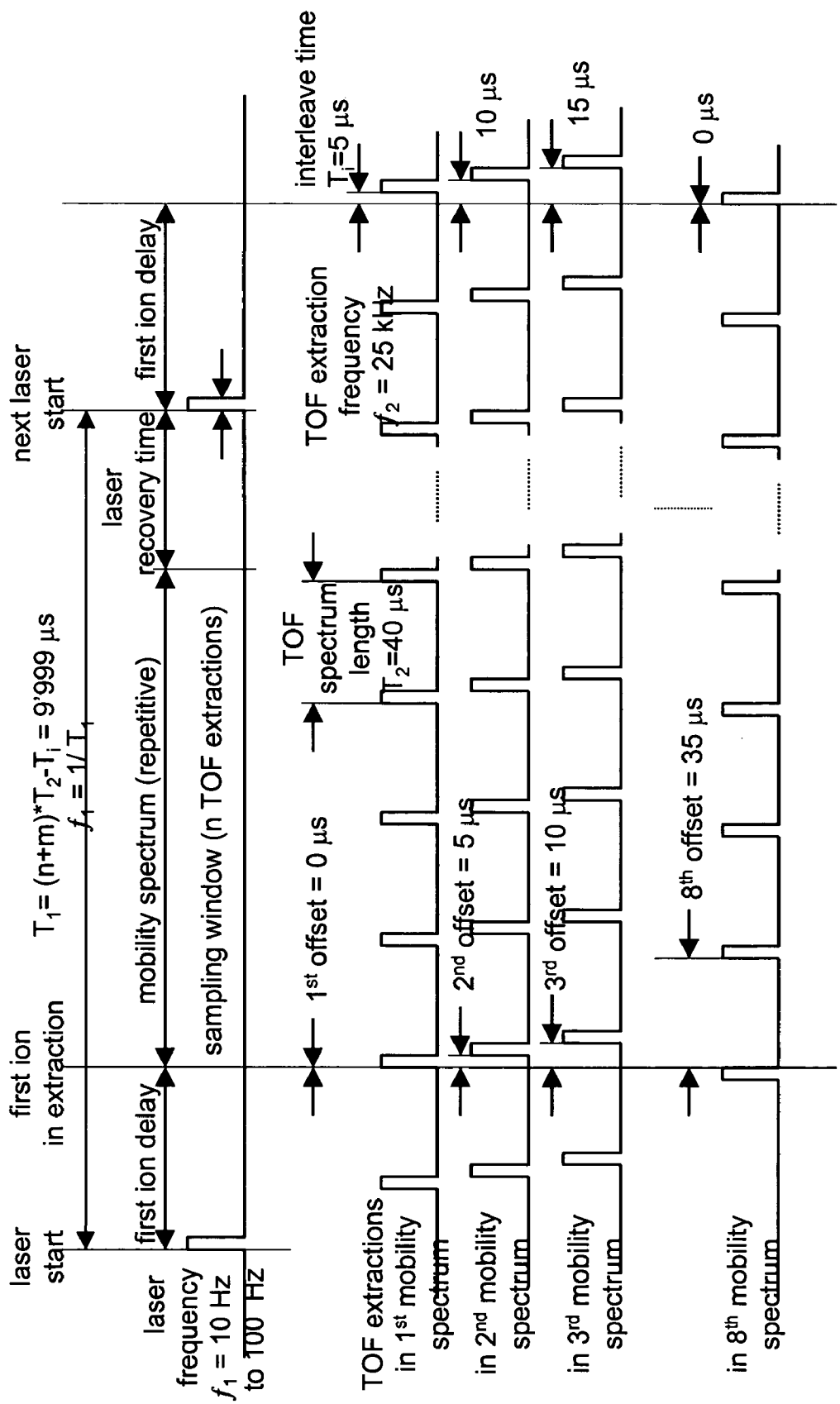
FIG. 3. A more detailed illustration of the timing scheme of the interleaved TOF acquisition.

Instruments employing either the interleaved method, the position sensitive detector method, or a combination of both, require a source of ions. In some cases, the temporal development of the ion generation itself is analyzed. For example, the kinetics of the formation of a chemical ion species during a discharge may be investigated. In other cases, a chemical or physical process that does not generate ions but only neutral particles may be under investigation. In this case these neutral particles will have to be ionized for the analysis. The analysis of neutral species in a chemical reaction is an example for such an application. In still another case, the temporal release of existing ions may be of interest. This is, for example, the case in an ion mobility spectrometer wherein the temporal elution of ions at the end of the mobility spectrometer is monitored in order to get information about the mobility of these ions. Any and all instruments and methods for creating or releasing ions are collectively referred to as "ion sources" herein. An example of an interleaved timing sequence is illustrated in FIGS. 2 and 3 may be used with the basic instrumental platform of the present invention as illustrated in FIG. 1. One of skill in the art knows how to determine a proper interleaved timing sequence and how to design or modify a interleaved timing sequence to achieve any particular desired results. The only variable is the pulsing scheme that is generated by the timing controller (60). The interleaved timing scheme is applicable in situations where a repetitive process must be mass analyzed. FIG. 1 is the specific case wherein a mobility spectrometer (2) is used as the source of such an ion process. Some ion mobility spectrometers separate ions on a very short time scale; i.e., just a few microseconds. Hence, to identify the ions eluting from the ion mobility spectrometer, the TOF has to detect those ions and resolve their mobility drift time. In FIG. 1, the ions eluting from the IMS are accelerated immediately into a primary beam (4) of an energy of 20 to 200 eV in order to minimize the time to travel from the IMS exit orifice (24) to the TOF extraction chamber (31). The ions then pass through the extraction chamber. When the timing controller (60) issues an ion extraction, the ion will be mass analyzed and its mobility drift time is identified with the time at which the extraction occurs. The interleaved timing scheme allows the scanning of the ions in the primary beam (4). An ion species that passed through the extractor without being extracted and detected in one mobility spectrum will be detected in a following mobility spectrum. This is accomplished by varying the time offset between the start of the mobility process at (1) and the TOF extraction sequence at (31), as illustrated in FIG. 2.

There are variations available in the operation of the ion extractor (i.e., the extraction chamber) (31). In FIG. 1, an orthogonal extractor is illustrated. An orthogonal extractor extracts the ions in orthogonal direction to their initial flight direction in the primary ion beam (4). Other types of TOF function with a coaxial extraction. For example, the interleaved method works with both orthogonal and coaxial extractors. The ion extractor of FIG. 1 uses a double pulsed extractor. In this embodiment, the back plate of the extraction chamber as well as the second grid are pulsed by a high voltage pulser (61). In other extraction chambers, only one electrode is pulsed, e.g. only the back plate or only the first grid. Alternatively, the ions are not extracted by a pulsed electric field, but by a fast creation of the ions within the extractor (31). In this case, the electric field is always present, and the particles enter the extraction region (31) as neutrals. A pulsed ionizing beam, e.g. an electron beam or a laser beam, is then used to simultaneously create and extract the ions. In other embodiments, the extracting field is slightly delayed with respect to the ion generation step in order to improve the time focusing properties of the TOF instrument.

The ion detector is used to create the stop signal of the time-of-flight measurement. The most common detectors used in TOF are electron multiplier detectors, where the ion to be detected generates one or several electrons by collision with an active surface. An acceleration and secondary electron production process then multiplies each electron. This electron multiplication cycle is repeated several times until the resulting electron current is large enough to be detected by conventional electronics. Some more exotic detectors detect the ion energy deposited in a surface when the ion impinges on the detector. Some other detectors make use of the signal electrically induced by the ion in an electrode. Any and all of these apparatuses and corresponding methods of ion detection, which are discussed in detail in the literature and known to those of ordinary skill in the art, are collectively referred to as "ion detector".

Two different and independent methods (as well as their combination) for obtaining high time resolving power for ion analysis by TOF are disclosed. The first method includes an interleaved timing scheme and the second method uses a position sensitive detector. Both of these methods allow one to obtain temporal information of the fast ion processes.

1) Interleaved Method:

An interleaved timing scheme is illustrated in FIGS. 2 and 3 and may be used with the instrumental platform shown in FIG. 1. One of skill in the art knows how to determine a proper interleaved timing sequence and how to design or modify a interleaved timing sequence to achieve any particular desired results. The critical variable is the pulsing scheme that is generated by the timing controller (60). The interleaved timing scheme is applicable to mass analysis of any repetitive process. FIG. 1 shows the ion output of a mobility spectrometer (2) is such a process. The pressures in the ion mobility region (2) are typically a few Torr to approximately atmospheric pressures. Some ion mobility spectrometers separate ions on a very short time scale i.e., less than 100 µs. Hence, to identify the ions eluting from the ion mobility spectrometer, the TOF has to detect those ions and resolve their mobility drift time. The ions eluting from the IMS through an orifice (24) are accelerated immediately into a primary beam (4) to a energy of 20 to 200 eV in order to minimize the time to travel from the IMS exit orifice (24) to the TOF extraction chamber (31). The pressure in region (4) is typically on the order of $10^{-4}$ Torr. The ions then enter the TOF extraction chamber (31). When the timing controller (60) issues an ion extraction, the ions will be mass analyzed in flight tube (33) and their mobility drift time is identified with the time at which the extraction occurred. The pressures in the flight tube region are typically on the order of $10^{-6}$ Torr. The interleaved timing scheme allows scanning the primary beam ion arrival times in the extraction chamber (31) relative to the time they were generated in the ion source (1). Ion species that pass through the extractor without being extracted and detected in one mobility spectrum will be detected in a following mobility spectrum. This is accomplished by variation of the time offset between the start of the mobility process (1) and the TOF extraction sequence, as illustrated in FIG. 2 and FIG. 3. FIG. 2 illustrates how the offset between the ion production (by laser) and the ion extraction sequence is increased by 5 µs (the interleaved time) for each ion production cycle. FIG. 3 illustrates the same sequence in greater detail. Here, the time delay until the first ion exits the mobility chamber is also indicated, as well as a laser recovery time, e.g., the time between the end of the mobility spectrum and the time at which a new laser pulse can be issued. The laser recovery time is largely time lost during the delay for the laser to recover for a new ion production cycle. The laser recovery time is variable. One skilled in the art recognizes that the laser recovery time is dependent upon the specific laser used. In general, times shown in the figures are illustrative and a number of lasers exhibiting a wide range of recovery times may be used.

In general, the range of offset times extends from zero to the time between two extractions. This is illustrated schematically in FIG. 2. Ideally, the extraction frequency is maximized in order to maximize data collection. However, this is limited by the mass and energy of the ions of interest and the instrumental flight path length. Once an extraction frequency is chosen, the offset range is automatically determined, ranging from 0 to the time corresponding to one extraction cycle. Data collection is then modified by choosing a different step size of the offset (interleaved time) within the offset range. In order to insure that no part of the time profile of the process under study goes unmonitored, this step size cannot be larger than the maximum offset range. The smaller the step size, the greater the temporal resolution of the data, however, this comes at the expense of longer data collection times. For example, if the extraction frequency is 10 kHz, the time between two extractions is 100 µs. If, for example, a 5 step interleaved sequence is chosen within that range, the step size will be 20 µs. In this example, the offset pattern will be 0, 20, 40, 60, 80, 100 µs. An offset range of 0 to 1000 µs is expected to cover most ion processes, corresponding to extraction frequencies down to 1 kHz.

Figure 4:
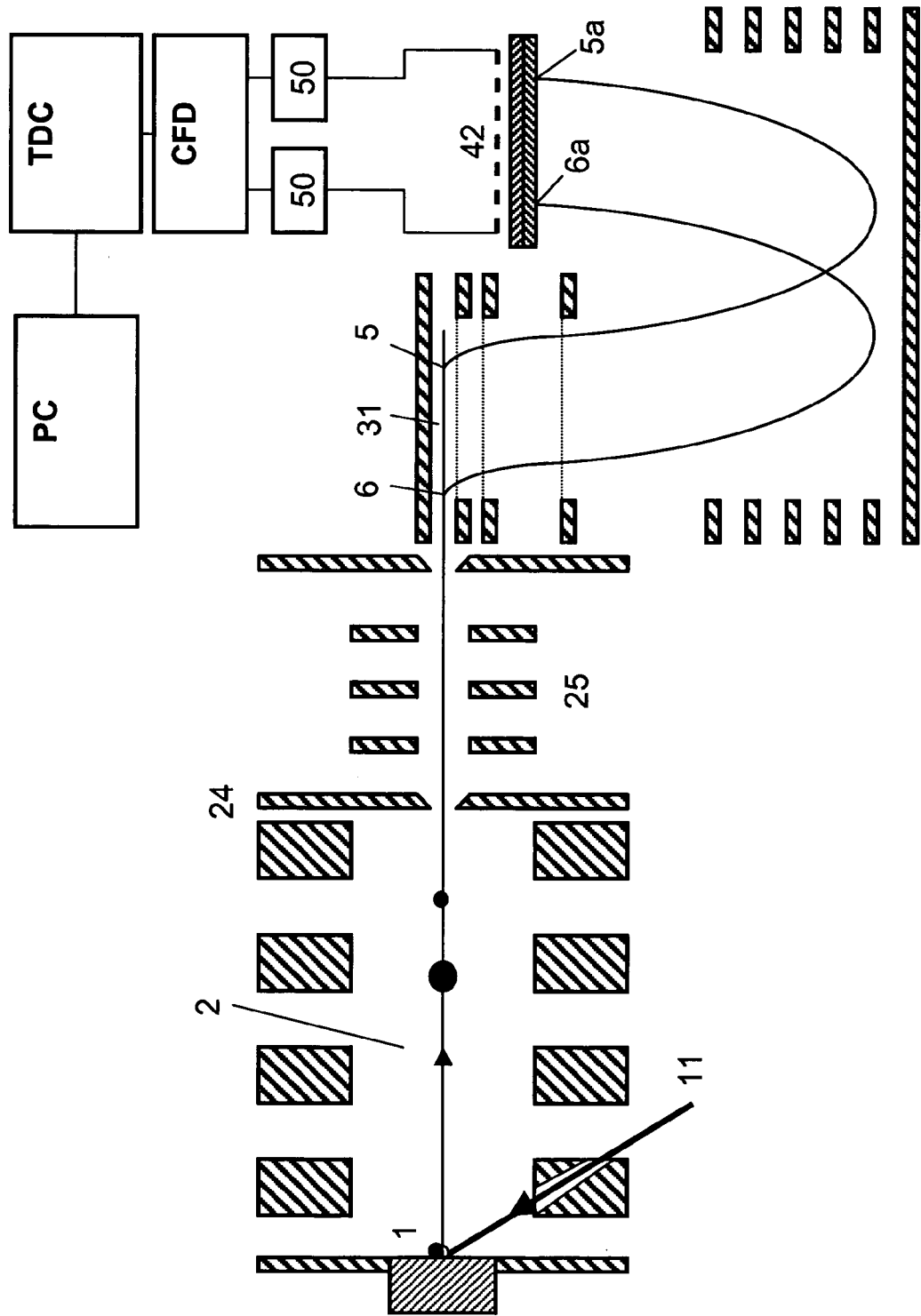
FIG. 4. Embodiment incorporating a delay-line position sensitive detector to the basic Mobility-TOF of FIG. 1 in order to distinguish ions arriving early to the ion extractor from those arriving at later times.

The smallest mobility drift time differences that can be detected with this method correspond to the "filling time" of the extraction chamber (31). This filling time is the time it takes an ion species to pass through the open extraction area. The differential filling time effect on ions entering the ion extractor at different times is illustrated in FIG. 4. An ion with a short mobility drift time will enter the extraction chamber early and at the time of extraction it will have moved in the extraction chamber to an extraction position (5). Another ion with a slightly longer mobility time will enter the extraction chamber later and at the moment of extraction it may be at a different position (6). The mobility drift time of those two ions cannot be distinguished easily with instruments of the prior art; applying an interleaved timing mode helps to alleviate this problem.

2) The PSD Method (Position Sensitive Ion Detection)

Figure 5:
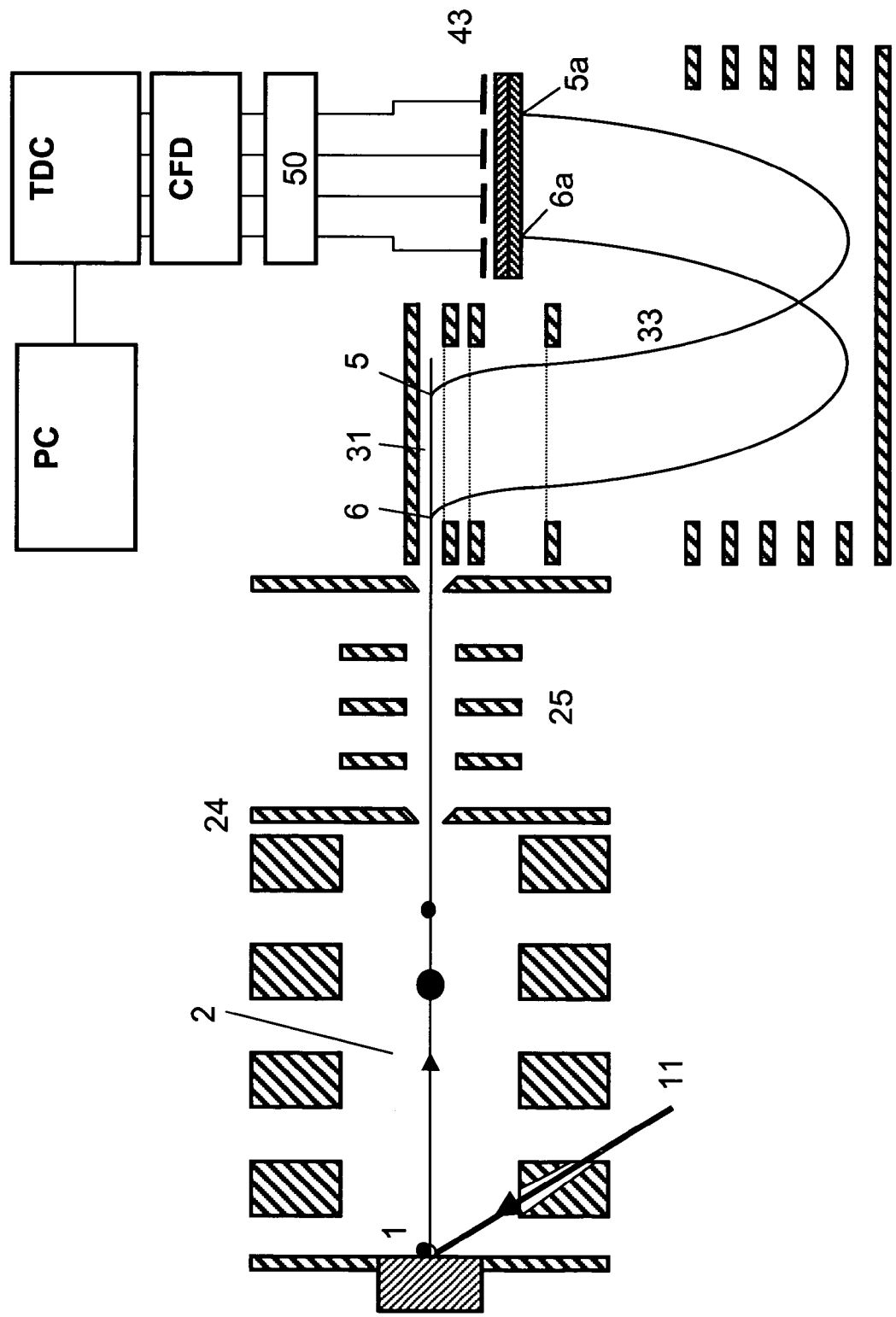
FIG. 5. Embodiment incorporating a multi-anode position sensitive detector to the basic Mobility-TOF of FIG. 1 in order to distinguish ions arriving early to the ion extractor from those arriving at later times.

The instruments shown in FIGS. 4 and 5 include position sensitive ion detectors (42) and (43), respectively, which allow one to distinguish between the ion extracted at a first position (5) and the ion extracted at a second position (6). The ability to distinguish these ions is based upon the different locations at which these ions impinge upon the detector. These different locations are schematically shown as (5a) and (6a), respectively. The use of the position sensitive ion detector (42) and (43) in FIGS. 4 and 5, respectively, improves the time resolution to less than the extraction fill time. The detector (43) of FIG. 5 is a multi-anode detector with limited position resolving capabilities but high count rate capabilities. Detector (42) of FIG. 4 is a meander delay line based position sensitive ion detector (see U.S. Pat. No. 5,644,128 of Wollnik; expressly incorporated by reference herein) with high position resolving power in at least one dimension, but with limited count rate capability. The preferred embodiment of the present invention would utilize a combination of these two detectors by using several delay line anodes (multiple meander delay lines) in order to obtain good position resolving power and high count rate capability.

The primary disadvantage of using this method with position sensitive ion detectors is their mass dependent resolution. Heavier ions are slower; hence their fill time is longer compared to the fill time of lighter ions. Heavier ions may not be able to travel far into the extraction chamber (31) before the next extraction occurs. For those ions it would be an advantage to have better position resolving power at the beginning of the detector. The following example illustrates the problem. Assuming that all primary beam ions (4) enter the extraction chamber (31) at more or less equal kinetic energies per charge (E/z), an ion of m/z=100 Thomson may have a fill time of 10 μs. In this case, a heavier ion with m/z=10,000 will have a fill time of 100 μs. Hence, at a 50 kHz extraction frequency which corresponds to one extraction every 20 μs, the 100 Thomson ions will overfill the extraction chamber, whereas the 10,000 Thomson ions will only fill the first ⅕th of the extraction chamber.

Figure 6:
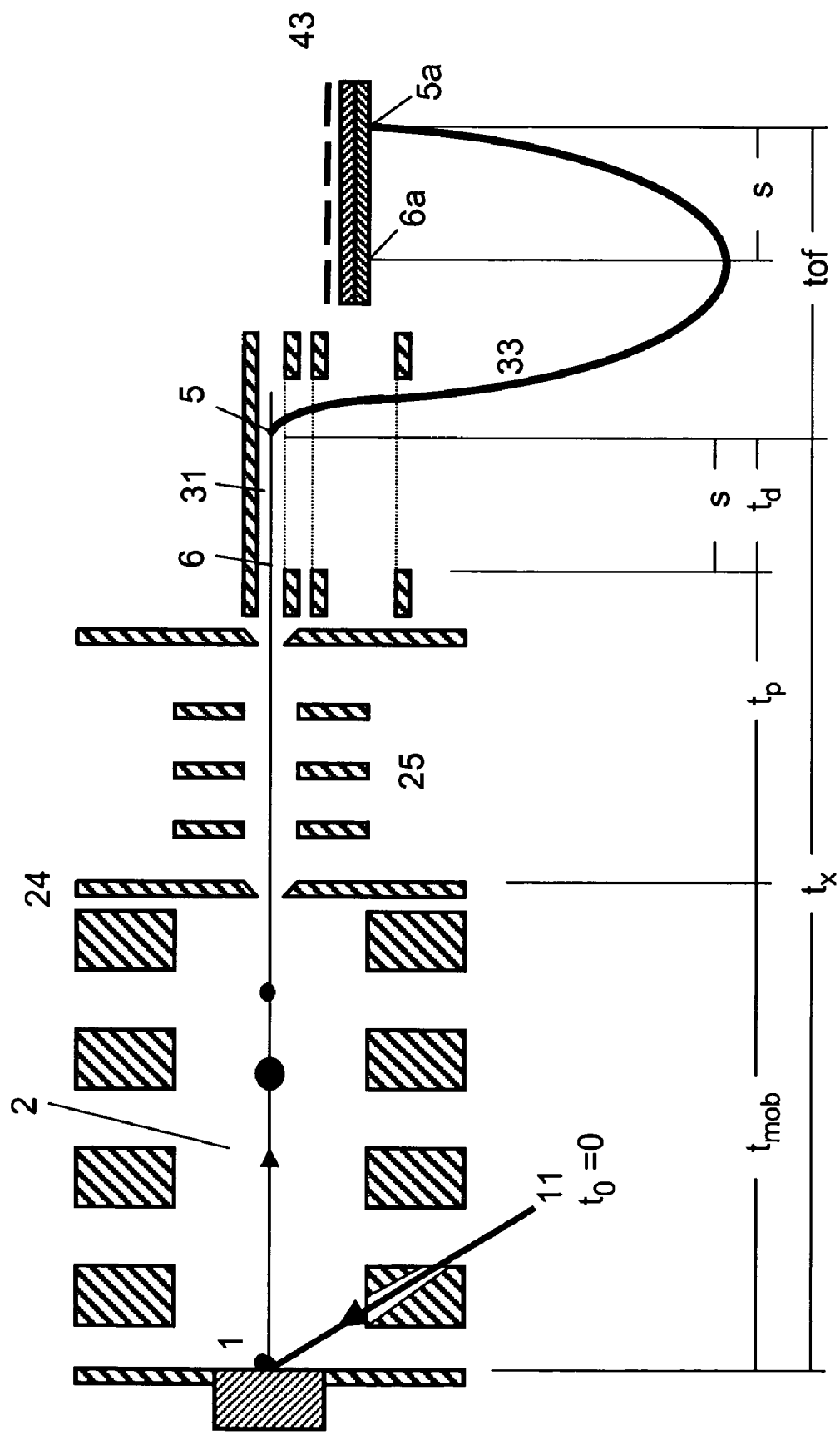
FIG. 6. Figure illustrating various ion transmission times and distances used in the governing equations in the Mobility-TOF of the invention.

In order to exploit the PSD fast acquisition method, the PSD requires a good position resolving capability in this first ⅕th of the detector (at position 6a). At the other end of the PSD (around position 5a), poorer position resolving capability may not be as detrimental to overall performance. FIG. 6 and the following mathematical treatment illustrates how the present invention allows one to reconstruct the mobility drift time $t_{mob}$ from the time of extraction to. The mobility process is initiated by a pulsed laser (11) at time t= 0. After the drift time $t_{mob}$ the ion appears at the exit orifice (24) of the mobility cell. From there it takes the ion a certain time, $t_p$ to travel to the beginning (6) of the open area in the extraction chamber (31). There, the ion passes through the extraction chamber (31) for a certain time $t_d$ until at time $t_x$ an extraction occurs. At that time, the ion is at position (5), which is the length s further inside the beginning (6) of the open area in the extraction chamber (31). This position is monitored with the position sensitive ion detector (43). Hence the mobility drift time is:

$$t_{mob}=t_x-t_d-t_p \quad (1)$$

where $$t_d = \sqrt{\frac{m}{2E}} \cdot s = \sqrt{\frac{m}{2zU}} \cdot s = a \cdot s \cdot \sqrt{\frac{m}{z}}. \quad (2)$$

where E is the kinetic energy of the particle in question and U is the acceleration voltage which gave the particle the energy, E.

If the initial velocities of the ions exiting from the mobility drift chamber are neglected, $$t_p = b \cdot \sqrt{m/z} \quad (3)$$

m/z is derived from the TOF measurement by $$m/z = c \cdot tof^2 + d \quad (4)$$

Figure 7:
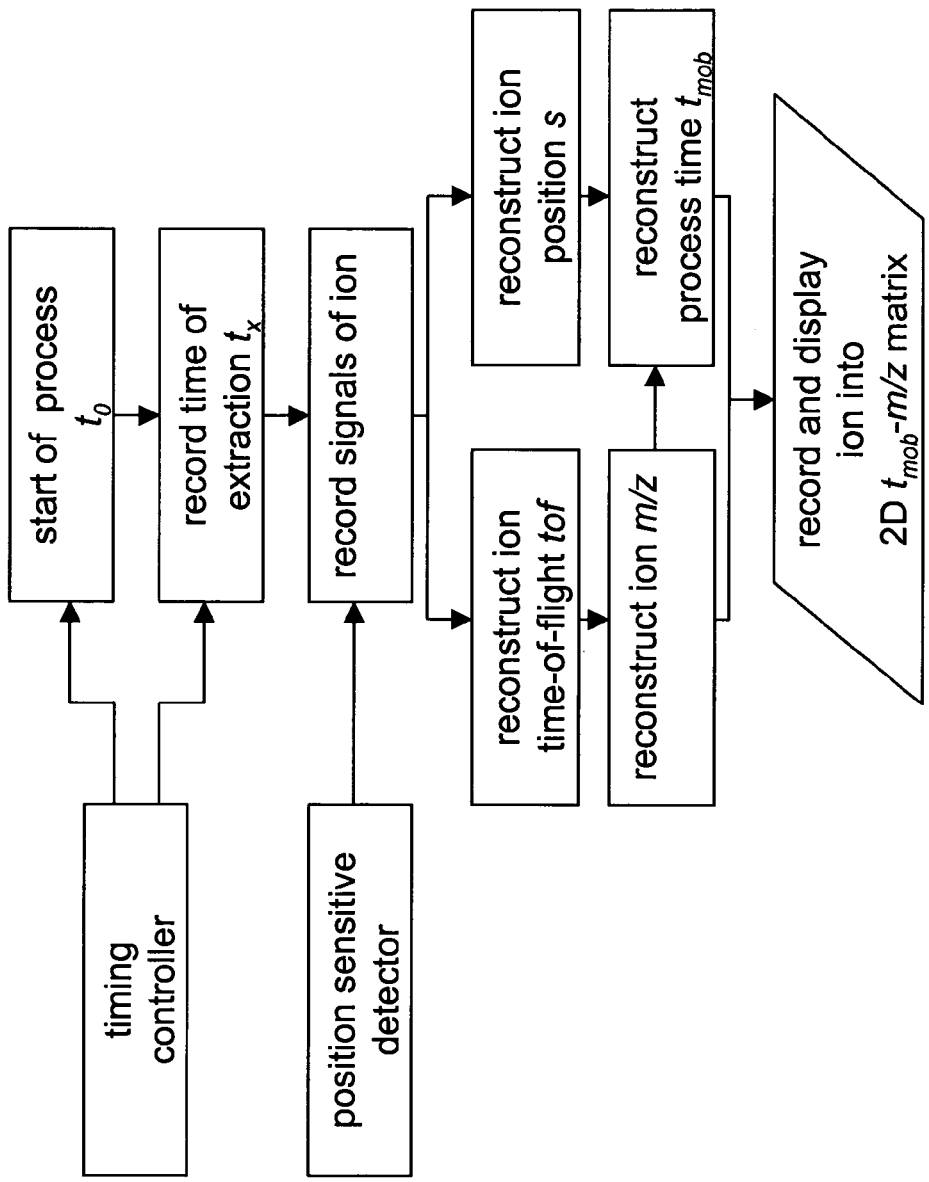
FIG. 7. Flow diagram illustrating the scheme for the reconstruction of the process time of an ion from the extraction time, and the ion m/z.

The parameters a, b, c and d are instrumental parameters that depend on the TOF geometry and the potentials applied. Once those parameters are known, the mobility time $t_{mob}$ can be calculated with the m/z information from the time-of-flight measurement and the distance s information from position sensitive ion detector with the process indicated in FIG. 7. For each ion, the process time, $t_{mob}$, which is the time of interest, can be calculated with the process start time to, the extraction time $t_x$, the ion position s, and the ion m/z by applying equations (1) to (4). FIG. 7 also illustrates how $t_0$ and $t_x$ are determined using the corresponding signals from the timing controller, whereas the position information s and the ion time-of-flight tof (eqn. 4) are derived from signals produced by the PSD.

Parameter c, d have to be obtained through calibration of the mass spectrum by assigning two known—mass peaks—which is a standard TOF calibration procedure. How to determine parameter b is less obvious.

In a preferred embodiment the parameter b is determined by $$b=t_p/\sqrt{m/z}$$

for one specific m/z for which $$t_p=t_x-t_{mob}-t_d$$

where $t_d$ is calculated as described above, $t_x$ is known by keeping track of the number of extractions with regard to the start of the ions in the ion source, and $t_{mob}$ is determined by varying the field strength E in the mobility cell while not changing the potentials from the skimmer to the detector. L is the length of the mobility cell. For each field strength E the time $(t_x+t_d)$ is recorded for the specific m/z. $L/(t_x+t_d)$ is plotted against the field strength. The slope of this plot equals K, and $t_{mob}$ for the specific m/z is then determined by $$t_{mob} = \frac{L}{K \cdot E}$$

Parameter b can then be used for the whole mass range, as long as no operating parameters are changed.

Alternatively the parameter b can be determined by calculating or simulating the flight time $t_p$ based on the actual potentials between the skimmer and the TOF extraction region.

This treatment is applicable not only for IMS-TOF combinations, but for the monitoring of any fast processes.

In a preferred embodiment, the transit time, $t_p$, is reduced by reducing the distance between the mobility cell exit (24) and the beginning of the open extractor area (6), and by accelerating the ions within this region. As a result, the differences in the transit time $t_p$ may become insignificant and the parameter b may remain unknown. In other words, instead of determining the mobility time, $t_{mob}$ it is often sufficient to determine the time $t_{mob}+t_p$.

Equation (3) also indicates that for ions with large m/z, the penetration into the extraction chamber is slow. Many of the larger ions will experience extraction early upon entry into the extraction chamber. A multi-anode detector configuration is helpful in improving position resolving power. Further, when using a multi-anode position sensitive detector (43), it is desirable to have smaller anodes in the area (6a) in order to increase the position resolving power for large m/z ions impinging in this area. This will maintain a process time resolving power for those large m/z ions. One skilled in the art recognizes that larger m/z ions will travel slowly from position (6) to position (5) than would smaller m/z ions. Potentially, these slower traveling ions may never reach position (5) because a new extraction event will occur before this time.

In the special case of monitoring the elution from a mobility cell, light ions will always appear in the extraction chamber early and heavier ions will appear later. This is because there is a strong correlation between ion mobility elution time and ion mass. Hence it is possible to increase the ion energy in the primary beam (4) (FIG. 1) during the elution of the mobility spectrum in this case so that the ion velocity in the primary beam stays approximately constant. Ramping up an accelerating potential somewhere in the primary beam optics (25) accomplishes this. In this way, the full area of the position sensitive ion detector is used at any time. This velocity correction method, however, cannot be used with IMS/IFP/MS. IMS/IFP/MS is the tandem method where ions are fragmented after the mobility separation, e.g. in region (25), prior to the TOF extraction. This fragmentation may be induced by gas collisions, by collisions with surfaces, or by bombardment with fragmenting beams i.e., an electron or photon beam. In this case, the correlation between mobility and mass is lost due to the fragmentation process creating light ions from ions with low mobility.

One example of a TOF instrument with PSD detection is as follows. An ion source repetitively generates ions. Ions from the ion source enter an ion extractor which extracts ions for time-of-flight measurement in a time-of-flight mass spectrometer. The ion extractor is fluidly coupled to the ion source. A position sensitive ion detector is fluidly coupled to the time-of-flight mass spectrometer to detect the ions issuing from it. A timing controller is in electronic communication with the ion source and the ion extractor and tracks and controls the time of activation of the ion source and activates the ion extractor according to a predetermined sequence. A data processing unit for analyzing and presenting data said data processing unit is in electronic communication with the ion source, the ion extractor, and the detector.

The TOF/PSD instrument can be modified to incorporate an interleaved timing scheme to produce an interleaved TOF/PSD instrument. This is accomplished by including a time offset between the activation of the ion source and the activation of the ion extractor. The time offset may be variable. Typical time offset ranges are from 0 to 1000 μs. The interleaved/PSD combination would yield instruments and methods having the advantages of both technologies. The position sensitive ion detection method can be used in any TOF design with spatial imaging properties, e.g. a linear TOF design or in a TOF design with multiple reflections.

Alternatively, the instrument of the previous paragraph could be modified to replace the PSD with an ion detector lacking position sensitivity. The result would be an interleaved-TOF instrument. While lacking the benefits of the PSD, such an instrument may be acceptable for analyses involving ions having a narrow spread of generation times.

The TOF/PSD instrument can possess a number of different features and variations. An adjustment means for adjusting the kinetic energies of the ions upon entering said extractor according to their mass. The PSD may be based upon the meander delay line technique. Such a meander delay line detector may have multiple meander delay lines. The position sensitive ion detector may have also multiple anodes. If a multiple anode detector is used, it may have anodes of the same or differing sizes.

Analytical methods can be based on the TOF/PSD instrument to determine the temporal profile of fast ion processes. This is accomplished by generating ions in an ion source, tracking the time of ion generation by a timing controller, and activating the extraction of the ions in a single or repetitive manner according to a predetermined sequence. The extracted ions are then separated in a time-of-flight mass spectrometer and detected with a position sensitive ion detector capable of resolving the location of impact of the ions onto the detector. The ions are then analyzed to determine the time characteristics of the fast ion processes from the ion impact location information, the time from the step of tracking, and the time of activation of the extractor. The temporal profile of the fast ion processes is thus determined.

In methods employing interleaved timing in addition to the TOF/PSD measurement, the steps of generating and activating extraction include a time offset between them. The time offset may be varied. Typical time offset ranges are from 0 to 1000 μs.

Alternatively, the method of the previous paragraph could be modified to replace the PSD with an ion detector lacking position sensitivity. The result would be an interleaved-TOF method. While lacking the benefits of analogous methodology employing a PSD, these methods may be acceptable for analyses involving ions having a narrow spread of generation times.

Variations and additional features to this general method are possible. In a specific embodiment, the kinetic energy of the ions is adjusted before the ion extraction. The position sensitive ion detector may be a meander delay line detector. It may have multiple meander delay lines. The position sensitive ion detector may comprise multiple anodes, wherein the multiple anodes may be of the same or different sizes.

Importantly, each instrument and method can be applied to any fast separation process, not being limited to IMS and can be used with ADC (analog-to-digital converter) or TDC (time-to-digital converter) detection schemes.

More specifically, the IMS may be replaced by a TOF, resulting in a TOF/TOF tandem mass spectrometer. As described above for the IMS/TOF, an ion collision method can be placed between the first TOF and the second TOF, thereby allowing for simultaneously analyzing fragments of several or all parent ions, exactly analogous to the IMS/TOF described above.

Figure 8B:
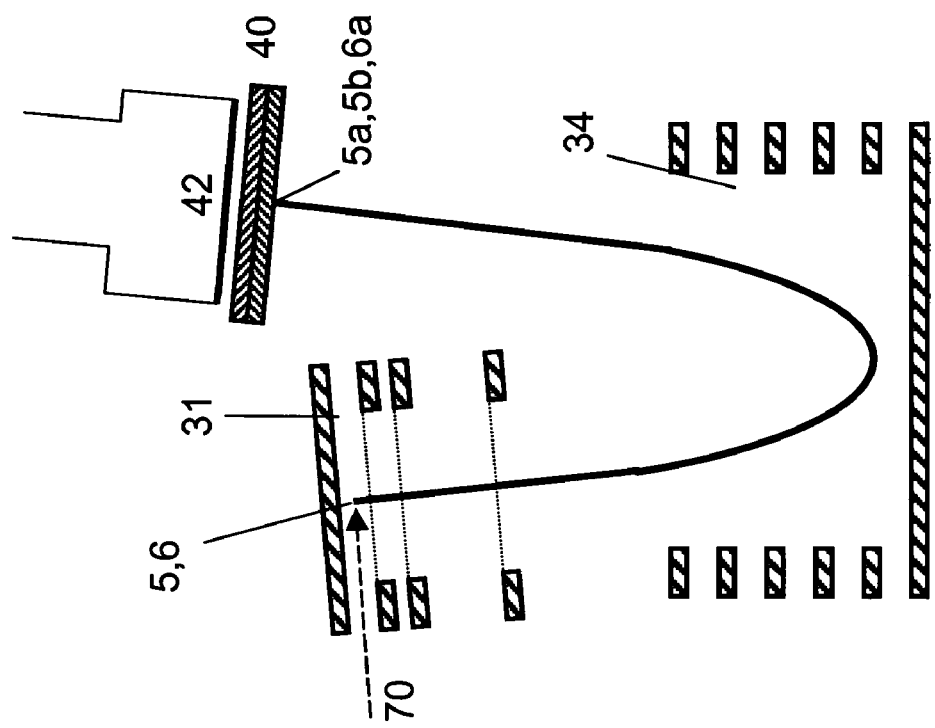
FIG. 8. TOF configuration for increased ion detection efficiency.
Figure 8A:
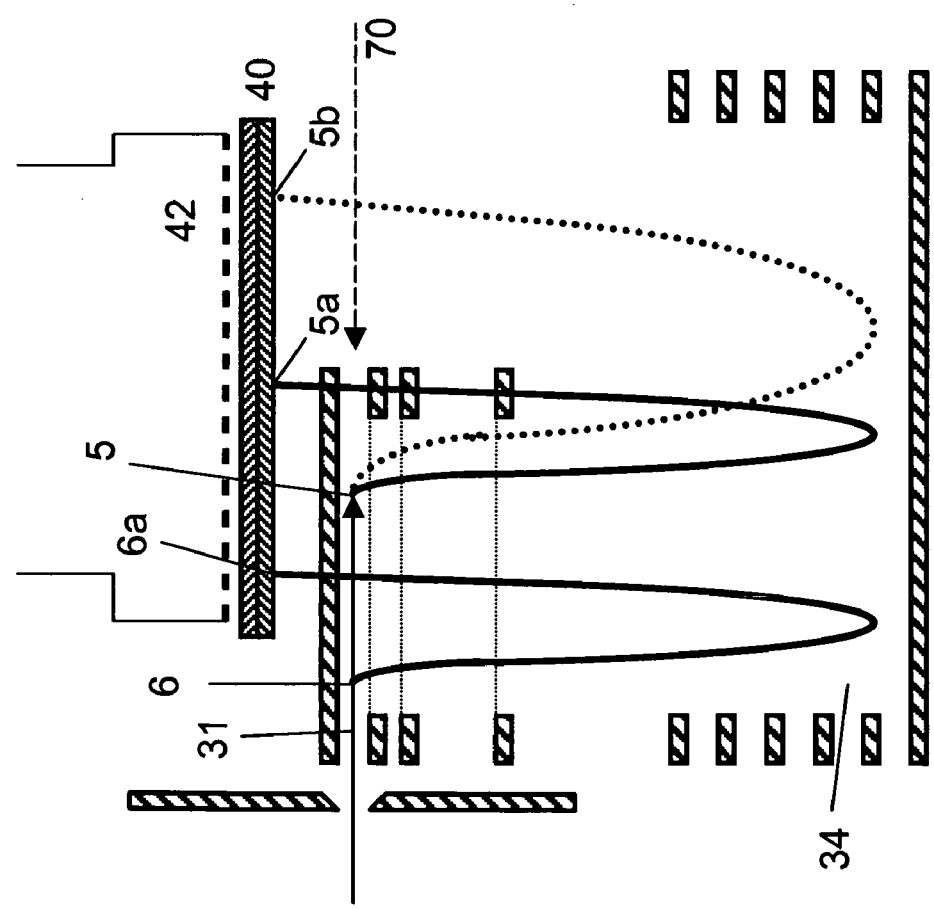

FIG. 8 shows an alternative embodiment where the extractor (31) and the detector 40 are not "in-line" as in FIGS. 1, 4, 5, and 6, but instead are positioned beside each other (FIG. 8A is a side-view; FIG. 6B is a view from the direction of the primary beam). If a grided reflector is used, the extractor (31) and the detector (40) should be tilted relative to the reflector (34). If a gridless reflector is used it is possible to find configurations tilting either the extractor or the detector. The advantage of this configuration is that a very long extractor as well as a long detector can be used even without excessive primary beam energies, and hence more ions can be detected. This is especially useful if the ions in the primary beam do not have equal energies, as indicated by two ions starting at position (5). The ion with the higher primary energy will follow the dashed flight path to the detector position (5b), whereas the lower energy ion will impact onto the detector at position (5a).

The ion transmission of the TOF (number of initial ions in the primary beam divided by the number of ions detected on the ion detector) is dependent on the ion mass, the energy of the ions in the primary beam, the extraction frequency and the extractor and detector energy. The longer the distance between the extractor and the detector (in longitudinal direction), the lower the ion transmission. By placing the extractor and the detector beside each other, this distance can be minimized. This configuration therefore results in an increase of the ion transmission by eliminating losses incurred when the extractor and detector are in line with each other and separated by a physical gap along the trajectory defined by the primary ion beam before the orthogonal extraction is applied.

Figure 9B:
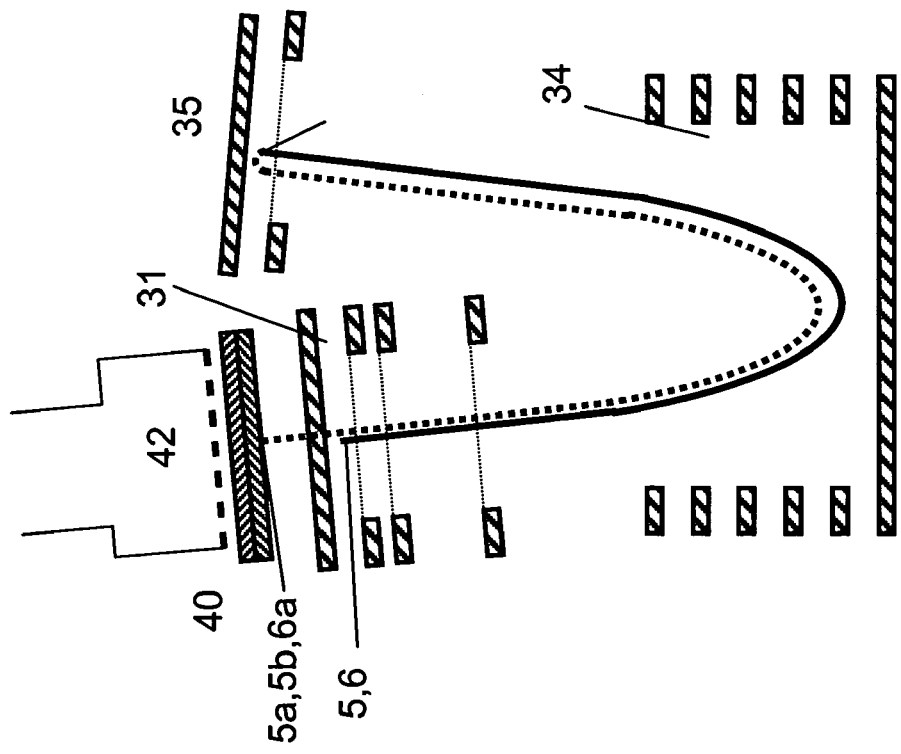
FIG. 9. Multi reflection TOF configuration for increasing the ion transmission.
Figure 9A:
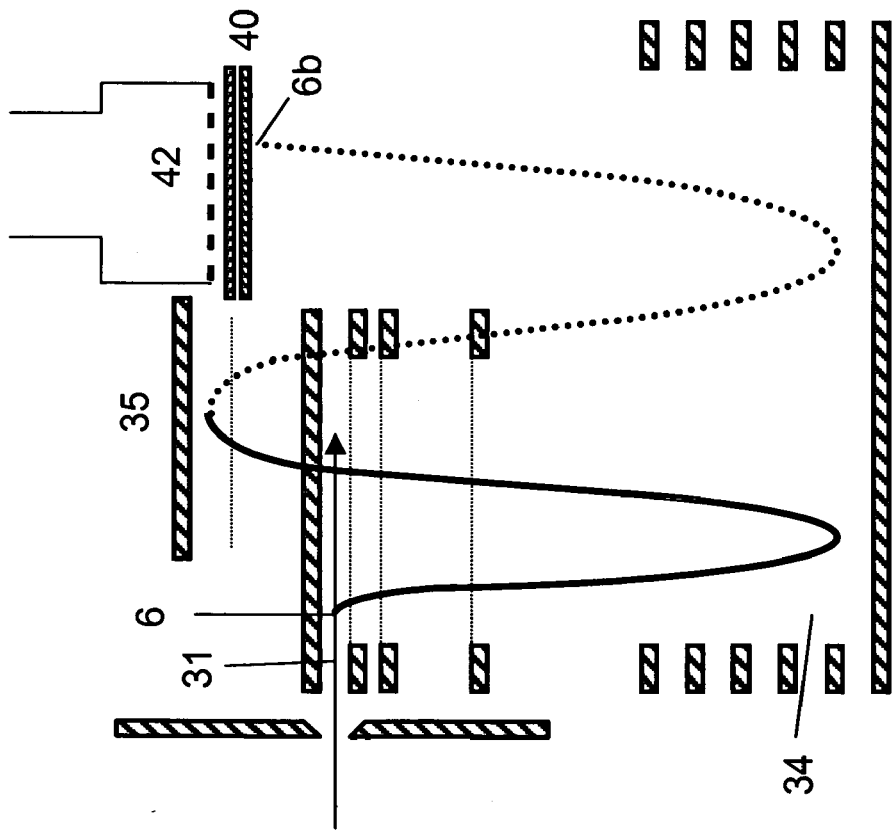

The tilted extraction is especially useful when a multi-reflection TOF is used. In such a case, the distance between extractor and detector is usually further increased due to an additional ion reflector (35) (also called hard mirror) traditionally positioned in line between extractor and detector. With a tilted extraction, however, the additional reflector (35) can be placed besides the detector and the extractor, thereby eliminating the need to increase the distance between extractor and reflector (FIG. 9). Again, with a gridless reflector (34), it is even possible to find configurations where the hard mirror (35) can be placed beside the extractor and detector without the need of tilting.

The ions may be fragmented within the primary beam in the extraction region (31) by a fragmentation beam (70) directly before extraction into the TOF. This may be accomplished by laser fragmentation, surface induced dissociation, collision induced dissociation, or any other known method to fragment ions; the preferred embodiment is a laser fragmentation pulse. The tilted extraction and detector setup allows detecting of both the less energetic fragment ions and the parent ions. This scheme also allows detection of all the ions exiting the mobility cell except for those above the frame of the extractor cell. This is helpful because one can achieve near 100% duty cycle.

Implementation of a 2D position sensitive detector would also allow discrimination of ions which are fragmented in the extraction region from those which will decompose from metastable species whose lifetime immediately during and after the photo-fragmentation event can be up to several microseconds. This will cause these species to fragment in the drift region. Delaying the extraction pulse some time after the laser fragmentation pulse (70) can enable the measurement of this lifetime and eliminate this broadening effect on the mass resolution of the daughter ions.

It has been found experimentally that the resolving power in the center region of a detector is higher than that close to the border of the detector. With a PSD this phenomenon can be exploited for using data recorded in the center of a detector for enhancing the evaluation of data from other regions of the detector. A first method uses peak information (especially peak position information) for deconvoluting peaks from other detector regions where peaks are more overlapping and where peak deconvolution is not possible without prior knowledge of peak data. With this method, the resolving power of TOF instruments using PSD can be further improved. In a second (very similar) method, peak information obtained in regions with good mass resolving power is used in fitting procedures applied to spectra obtained from detector regions with decreased resolving power.

The mobility pre-separation allows an improvement in the ability to collisonially dissociate large molecules by fluidly or stepwise increasing the voltage between the skimmer and the extraction optics as the mass along a particular trend line increases. Larger ions require higher voltages than do smaller ones for efficient fragmentation. However, the consequence of this is that the extraction pulse and the reflector voltage will have to be scanned proportionately, which may complicate mass calibration.

One way to perform this calibration is by laser desorbing pure $C_{60}$ fullerenes which gives well produced $C_2$ losses from monomer, dimer, trimers and tetramers in the region of a few hundred a.m.u. through several thousand a.m.u. The calibration can be achieved by first obtaining the mobility/mass data with everything constant (as previously described) and then acquiring data with again but with the scanned voltages. The spectra of the known fullerene ions taken with constant voltages can then be compared to the one obtained with the scanned voltages. Any corrections to the scanned mode calibrations can then be determined in an iterative manner and fine adjusted. The scan rates (and calibrations) could then be calculated for different molecules (such as peptides) which appear in a different region of the mobility vs. m/z two dimensional plot. We would then further check the calibration accuracy using several peptides with known masses over the range of interest.

A further embodiment would use a noble gas resonance light source for photo-fragmenting or further ionizing the ions separated by the mobility cell but before they are orthogonally extracted into the TOF. Such a source filled with He gas can be made to emit large photon fluxes of either 21.2 eV and or 40.8 eV photons. Other noble gases may be used to create lower energy photons which may be desirably used either for enhancing or for de-emphasizing fragmentation processes versus photoionization of the mobility separated ions. The photons may either dissociate the mobility separated ions or they may further ionize the ions to create multiply charged ions. For example, this could be particularly desirable and chemically specific for peptide analysis since some peptides contain side chains such as sulfhydril or phosphorylated side chains which could preferentially be photoionized with a higher crosssection than any of the other constituents of the peptide structure. The resulting doubly ionized peptide would thus preferentially occur when the peptide contained an easily photoionizable side chain and the resulting doubly charge parent ion would retain the longitudinal velocity of the MH+ parent peptide mobility separated. Thus when both ions were orthogonally extracted the doubly charged parent would have a velocity which was faster than the MH+ parent by a factor of the square root of two. Thus the doubly ioinized parent molecule would hit the PSD at a predictable position which was not as far along the PSD as the position of impact of the singly ionized parent ion. This would allow discrimination of certain important side chains by a combination of accurate mass analysis of the singly and doubly charge ions and the propensity of certain side chains to preferentially ionize compared to the peptide as a whole. In other cases the structure of the mobility separated ion might dictate that the doubly charged ion was not stable and the dissociation would be into two charged fragments which could be detected in coincidence on different places on the PSD but from the same orthogonal extraction pulse.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patent References

| U.S. Pat. No. 5,905,258 | Clemmer et al. | May 18, 1999 |
| U.S. Pat. No. 5,644,128 | H. Wollnik et al | Jul. 1, 1997 |
| U.S. Pat. No. 4,472,631 | Enke et al. | Sep. 18, 1984 |
| WO 99/38191A2 | Bateman et al. | Jul. 29, 1999 |
| WO 99/67801A2 | Gonin | Dec. 29, 1999 |

OTHER PUBLICATIONS

C. Fockenberg, H. J. Bernstein, G. E. Hall, J. T. Muckerman, J. M. Preses, T. J. Sears, R. E. Weston, Repetitively samples time-of-flight spectrometry for gas-phase kinetics studies, Rev. Scientific Instruments 70/8 (1999) p. 2359.

D. C. Barbacci, D. H. Russel, J. A. Schultz, J. Holoceck, S. Ulrich, W. Burton, and M. Van Stipdonk, Multi-anode Detection in Electrospray Ionization Time-of-Flight Mass Spectrometry, J. Am. Soc. Mass Spectrom. 9 (1998) 1328–1333.

I. A. Lys, "Signal processing for Time-of-Flight Applications"; from "Time-Of-Flight Mass Spectrometry"; (ACS Symposium Series, No 549) by Robert J. Cotter (Editor).

What is claimed is:

1. An apparatus comprising:
    an ion source for repetitively generating ions;
    an ion-fragmentation device fluidly coupled to said ion source;
    an ion extractor, fluidly coupled to said ion fragmentation device and extracting said ions;
    a time-of-flight mass spectrometer fluidly coupled to and accepting ions from said ion extractor,
    a position sensitive ion detector fluidly coupled to said time-of-flight mass spectrometer to detect said ions;
    a timing controller in electronic communication with said ion source and said ion extractor said timing controller tracking and controlling the time of activation of said ion source and activating said ion extractor according to a predetermined sequence; and,
    a data processing unit for analyzing and presenting data said data processing unit in electronic communication with said ion source, said ion extractor, and said position sensitive ion detector.

2. The apparatus according to claim 1 wherein the ion fragmentation device is positioned to fragment ions at a location within the ion extractor or at a location before the ion extractor.

3. The apparatus according to claim 1 wherein said timing controller or said data processing unit or both are in electronic communication with said ion-fragmentation device.

4. A method of determining the temporal profile of fast ion processes comprising:
    generating ions in an ion source;
    tracking the time of said step of generating by a timing controller;
    fragmenting said ions to form fragment ions;
    extracting said ions and fragment ions in a single or repetitive manner according to a predetermined sequence;
    separating said extracted ions and fragment ions in a time-of-flight mass spectrometer;
    detecting said ions and fragment ions with a position sensitive ion detector capable of resolving the location of impact of said ions and fragment ions onto said detector;
    analyzing the time characteristics of said fast processes from said impact location, the time from the step of tracking, and the time of activation of said extractor to determine the temporal profile of the fast ion processes.

5. The method of claim 4 wherein the step of fragmenting said ions occurs in the ion extractor or up stream of the ion extractor.

6. The method of claim 4 wherein the step of analyzing further comprises analyzing the time characteristics of said fast processes using the time of activation of said step of fragmenting.

7. An apparatus comprising:
    an ion source capable of repetitively generating ions;
    an ion-fragmentation device fluidly coupled to the ion source and capable of generating fragment ions;
    an ion extractor, fluidly coupled to the ion-fragmentation device and extracting said ions and fragment ions;
    a time-of-flight mass spectrometer fluidly coupled to and accepting said ions and fragment ions from said ion extractor,
    an ion detector fluidly coupled to said time-of-flight mass spectrometer to detect said ions and fragment ions; and,
    a timing controller in electronic communication with said ion source and said ion extractor said timing controller tracking and controlling the time of activation of said ion source and activating said ion extractor according to a predetermined sequence said sequence having a repetitively variable time offset between the activation of said ion source and the activation of said ion extractor.

8. The apparatus according to claim 7 wherein the ion fragmentation device is positioned to fragment ions at a location within the ion extractor or at a location before the ion extractor.

9. The apparatus according to claim 7 wherein said timing controller is in electronic communication with said ion-fragmentation device.

10. A method of determining the temporal profile of fast ion processes comprising:
    generating ions from an ion source;
    extracting said ions in a single or repetitive manner;
    activating said step of generating ions and said step of extracting said ions by a timing controller wherein said timing controller operates according to a predetermined sequence and further wherein said timing controller operates by a repetitively variable time offset between said step of activating and said step of extracting;
    fragmenting said ions before they are extracted into the time-of-flight mass spectrometer
    separating the ions and fragment ions according to their time-of-flight in a time-of-flight mass spectrometer;
    detecting the mass separated ions and fragment ions;
    analyzing the time characteristics of said fast ion processes from the time of said steps of activating, extracting, and detecting to determine the temporal profile of the fast ion processes.

11. The method of claim 10 wherein the step of fragmenting said ions occurs in the ion extractor or upstream of the ion extractor.

12. The method of claim 10 wherein the step of analyzing further comprises analyzing the time characteristics of said fast processes using the time of activation of said step of fragmenting.

13. An apparatus comprising:

an ion source capable of repetitively generating ions;

an ion extractor, fluidly coupled to said ion source and extracting said ions for time-of-flight measurement;

a time-of-flight mass section fluidly coupled to and accepting ions from said ion extractor, an ion detector fluidly coupled to said time-of-flight mass section to detect said ions; and, a timing controller in electronic communication with said ion source and said ion extractor said timing controller tracking and controlling the time of activation of said ion source and activating said ion extractor according to a predetermined sequence said sequence having a repetitively variable time offset between the activation of said ion source and the activation of said ion extractor.

14. A method of determining the temporal profile of fast ion processes comprising:

generating ions from an ion source;

extracting said ions in a single or repetitive manner;

activating said step of generating ions and said step of extracting said ions by a timing controller wherein said timing controller operates according to a predetermined sequence and further wherein said timing controller operates by a repetitively variable time offset between said step of activating and said step of extracting;

separating the ions according to their time-of-flight in a time-of-flight mass section;

detecting the mass separated ions; and, analyzing the time characteristics of said fast ion processes from the time of said steps of activating, extracting, and detecting to determine the temporal profile of the fast ion processes.

* * * * *